(12) United States Patent
Assanelli et al.

(10) Patent No.: US 10,087,163 B2
(45) Date of Patent: Oct. 2, 2018

(54) PROCESS FOR PREPARING CYCLIC ACETALS WHICH CAN BE USED AS FUEL COMPONENTS

(71) Applicant: ENI S.p.A., Rome (IT)

(72) Inventors: Giulio Assanelli, Pavia (IT); Alberto Renato De Angelis, Legnano (IT)

(73) Assignee: ENI S.p.A., Roma (IT)

( * ) Notice: Subject to any disclaimer, the term of this patent is extended or adjusted under 35 U.S.C. 154(b) by 0 days.

(21) Appl. No.: 15/302,819

(22) PCT Filed: Apr. 3, 2015

(86) PCT No.: PCT/IB2015/052466
§ 371 (c)(1),
(2) Date: Oct. 7, 2016

(87) PCT Pub. No.: WO2015/155659
PCT Pub. Date: Oct. 15, 2015

(65) Prior Publication Data
US 2017/0029401 A1 Feb. 2, 2017

(30) Foreign Application Priority Data
Apr. 7, 2014 (IT) .............................. MI2014A0633

(51) Int. Cl.
*C07D 317/12* (2006.01)
*C07D 317/26* (2006.01)
*C10L 1/185* (2006.01)

(52) U.S. Cl.
CPC ......... *C07D 317/12* (2013.01); *C07D 317/26* (2013.01); *C10L 1/1855* (2013.01); *C10L 2200/0469* (2013.01)

(58) Field of Classification Search
CPC ...... C07D 317/12; C07D 31/26; C07D 31/12; C07D 317/26; C10L 1/1855; C10L 2200/0469
See application file for complete search history.

(56) References Cited

U.S. PATENT DOCUMENTS

2015/0113860 A1 4/2015 De Angelis et al.

FOREIGN PATENT DOCUMENTS

WO WO 2013/150457 A1 10/2013

OTHER PUBLICATIONS

International Search Report and Written Opinion dated Jul. 10, 2015 in PCT/IB2015/052466.
Keitaro Mori et al., "Catalytic dehydration of 1,2-propanediol into propanal", Applied Catalysis A: General, Elsevier Science, vol. 366, No. 2, XP026520648, 2009, pp. 304-308.

*Primary Examiner* — Timothy R Rozof
(74) *Attorney, Agent, or Firm* — Oblon, McClelland, Maier & Neustadt, L.L.P.

(57) ABSTRACT

The present invention relates to a process for preparing cyclic acetals having general formula (I) wherein Y and Y', equal to or different from each other, are selected from H and a group OR, R being a linear or branched alkyl containing from 1 to 8 carbon atoms, comprising at least the following phases: (i) providing a reaction mixture comprising at least one vicinal diol having formula (II) Z—$CH_2$—CHOH—$CH_2$OH wherein Z is selected from H and a group OR', R' being a linear or branched alkyl containing from 1 to 8 carbon atoms, said mixture being substantially free of aldehydes having general formula $R^I$—CHO, wherein $R^I$ is a linear or branched alkyl containing from 1 to 6 carbon atoms, possibly substituted by an alkoxide group $OR_{111}$, wherein $R^{III}$ is an alkyl containing from 1 to 4 carbon atoms; (ii) thermally treating said reaction mixture at a temperature within the range of 100° C.-300° C. in the presence of at least one acid catalyst, obtaining said compound having formula (I). The acetals having formula (I) can be used as fuel components.

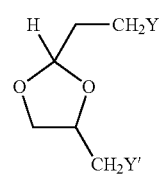

(I)

15 Claims, No Drawings

PROCESS FOR PREPARING CYCLIC ACETALS WHICH CAN BE USED AS FUEL COMPONENTS

The present invention relates to a process for preparing cyclic acetals, in particular starting from glycerine, which can be used, for example, as fuel components.

It is known that emissions produced by the combustion of fuels of a fossil origin, containing carbon dioxide ($CO_2$), carbon monoxide (CO), nitrogen oxides ($NO_x$), sulfur oxides ($SO_x$), unburned hydrocarbons (HC), volatile organic compounds and particulate (PM), are the cause of environmental problems such as, for example, reduction in the ozone layer, the greenhouse effect (in the case of nitrogen and carbon oxides) and acid rain (in the case of sulfur and nitrogen oxides).

Over the years, the increase in the cost of crude oil and a maturing awareness with respect to environmental problems, have reinforced the necessity of finding alternative energy sources, which are renewable and have a lower environmental impact.

Consequently, the progressive substitution of fuels deriving from fossil energy sources such as, for example, coal, petroleum, natural gas, with fuels deriving from alternative energy sources such as, for example, vegetable oils, animal fats, biomasses, algae, is becoming of increasing interest on a worldwide scale and efforts have therefore been made in the art to obtain new fuels from renewable energy sources.

An oxygenated compound, that can also be obtained from renewable sources, commonly used as fuel component, is ethanol. Ethanol, however, has the disadvantage of being miscible with water, hygroscopic, and immiscible with gasoil within a wide temperature range: phase separation can therefore take place and the mixtures obtained are unstable, as described, for example, by Lapuerta et al. in the article "Stability of diesel-bioethanol mixtures for use in diesel engines", published in "Fuel" (2007), Vol. 86, pages 1351-1357.

Another alcohol, that can also be obtained from renewable sources, which can be used as component to be added to fuels, is butanol. Butanol has a better miscibility with gasoil with respect to that of ethanol, but is still not completely satisfactory. At low temperatures, in fact, butanol-gasoil mixtures are not homogeneous.

A further problem linked to the use of these alcohols is the low cetane number of the alcohol-gasoil mixture which causes a high ignition delay in internal compression diesel engines.

In the field of the present invention, the use is also known of biodiesel and hydrotreated vegetable oils (HVO) as such, or in a mixture with gasoil, and also mixtures of gasoil comprising alcohols of a biological origin.

Biodiesel generally comprises a mixture of fatty acid alkyl esters, in particular a mixture of fatty acid methyl esters (FAME) and can be produced starting from raw materials of a natural origin containing triglycerides (triesters of glycerine with fatty acids having a long alkyl chain). Said raw materials as such, or the triglycerides obtained after subjecting said raw materials to separation, are subjected to a transesterification process with an alcohol, in particular, methanol, in the presence of a catalyst, so as to obtain said fatty acid alkyl esters (FAME).

FAME compounds, however, when used as such or in a mixture with gasoil, have a low stability to oxidation. Furthermore, their synthesis process is accompanied by the formation, as by-product, of significant quantities of glycerine (about 10% by weight with respect to the FAME product obtained), whose use is an important aspect for the development of the widespread use of biodiesel fuels.

The use is known of "hydrotreated vegetable oils" (HVOs), also called "green diesel", produced starting from raw materials obtained from renewable sources (e.g. soybean oil, rapeseed oil, corn oil, sunflower oil). HVOs are prepared by the hydrogenation/deoxygenation of the starting oils, which contain triglycerides and free fatty acids, with hydrogen in the presence of a catalyst, as described, for example, by Holmgren J. et al. in the article "New developments in renewable fuels offer more choices", published in "Hydrocarbon Processing", September 2007, pages 67-71. This article indicates the improved characteristics of said hydrotreated vegetable oils (HVOs) with respect to fatty acid methyl esters (FAMEs), in particular, in terms of a better oxidation stability and improved cold properties. Furthermore, HVOs do not have the problem of increased emissions of nitrogen oxides observed for FAMEs as they do not substantially contain oxygen atoms. Due to the lack of these oxygen atoms, however, the use of HVOs in diesel engines mixed with gasoil in an amount lower than 5% by volume with respect to the total volume of said mixture, does not provide significant benefits with respect to emissions of particulate (PM).

A considerable problem in the state of the art is the high production of glycerine as by-product of production processes of biofuels, in particular production processes of biodiesel and FAMEs. The necessity is therefore strongly felt for recovering said glycerine in excess, preferably for producing further fuel components.

At present, one of the possible uses of glycerine is to react it, by means of an etherification reaction, with olefins to give the corresponding ethers, which can be used as oxygenated components for fuels (both gasoline and diesel). The olefin mainly used is isobutene. The reaction with isobutene leads to the formation of tert-butyl ethers of glycerine, of which the most interesting is di-tert-butyl ether.

WO2013/150457 describes another possible use of glycerine in the field of the production of fuel components. This patent application describes hydrophic compounds belonging to the group of ketals and acetals having formula (A) and (B)

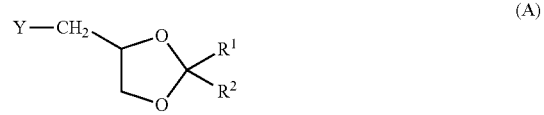

(A)

(B)

wherein:

$R^1$ is a linear or branched alkyl containing from 1 to 6 carbon atoms, possibly substituted by an alkoxide group OR, wherein R is an alkyl containing from 1 to 4 carbon atoms, $R^2$ is H or a linear or branched alkyl containing from 1 to 6 carbon atoms, possibly substituted by an alkoxide group OR, wherein R is an alkyl containing from 1 to 4 carbon atoms, $R^2$ is the same as or different from $R^1$, Y is selected from H or $OR^3$, $R^3$ being a linear or branched alkyl containing from 1 to 8 carbon atoms.

These compounds have a high affinity with respect to the hydrocarbon mixtures which typically form fuels and a low affinity for water. These compounds can be advantageously used as fuel components (e.g. gasoline or gasoil), as they are capable of reducing particulate emissions deriving from the combustion process, without significantly altering the specific characteristics of the fuel (for example, cloud point (CP)), cold filter plugging point" (CFPP), demulsivity, lubricity).

In WO2013/150457, the above compounds are prepared starting from glycerine by means of a process which comprises at least a first transformation step of the glycerine to propanediol or to an alkoxy-propanediol and a second step in which the propanediol or alkoxy-propanediol is reacted with an aldehyde or ketone to form the corresponding ketals and acetals. The aldehydes and ketones used in WO2013/150457 have general formula $R^I COR^{II}$ wherein:

$R^I$ is a linear or branched alkyl containing from 1 to 6 carbon atoms, possibly substituted by an alkoxide group $OR^{III}$, wherein $R^{III}$ is an alkyl containing from 1 to 4 carbon atoms;

$R^{II}$ is H or a linear or branched alkyl containing from 1 to 6 carbon atoms, possibly substituted by an alkoxide group $OR^{IV}$, $R^{IV}$ being an alkyl containing from 1 to 4 carbon atoms.

Although the process described in WO2013/150457 is characterized by excellent yields and selectivity towards the final ketals or acetals, it envisages in any case two reaction steps, with a significant consumption of chemical reagents (in particular, aldehydes and ketones) for obtaining the end-product; this naturally increases the overall production costs of these compounds.

The objective of the present invention is to overcome the drawbacks of the state of the art.

In particular, a specific objective of the present invention is to provide a process for the preparation of acetals and ketals which can be used, for example, as fuel components, which is simple to effect and entails a reduced consumption of chemical reagents.

In the light of this objective and others which will appear evident from the following description, a process is provided, in accordance with the present invention, for preparing at least one compound having general formula (I):

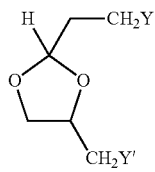

(I)

wherein Y and Y', equal to or different from each other, are selected from H and a group OR, R being a linear or branched alkyl containing from 1 to 8 carbon atoms, comprising at least the following phases:

(i) providing a reaction mixture comprising at least a vicinal diol having formula (II)

wherein Z is selected from H and a group OR', R' being a linear or branched alkyl containing from 1 to 8 carbon atoms, said mixture being substantially free of aldehydes having general formula $R^I$—CHO, wherein $R^I$ is a linear or branched alkyl containing from 1 to 6 carbon atoms, possibly substituted by an alkoxide group $OR^{III}$, wherein $R^{III}$ is an alkyl containing from 1 to 4 carbon atoms;

(ii) thermally treating said reaction mixture at a temperature within the range of 100° C.-300° C. in the presence of at least one acid catalyst, obtaining said compound having formula (I).

The Applicant has surprisingly found that acetals having formula (I) can be obtained through a simple thermal treatment of a vicinal diol in the presence of an acid catalyst, rather than reacting said vicinal diol with an aldehyde as proposed in the state of the art.

According to the present invention, in step (i) a reaction mixture is prepared, which comprises at least one vicinal diol having formula (II) and possible additional components. The reaction mixture is substantially free of aldehydes capable of reacting with said vicinal diol to give the above compounds having formula (I). In particular, the reaction mixture is substantially free of aldehydes having general formula $R^I$—CHO, wherein $R^I$ is a linear or branched alkyl containing from 1 to 6 carbon atoms, possibly substituted by an alkoxide group $OR^{III}$, wherein $R^{III}$ is an alkyl containing from 1 to 4 carbon atoms.

In a preferred embodiment, the reaction mixture is also substantially free of ketones, in particular ketones having general formula $R^I$—CO—$R^I$, wherein $R^I$ is as defined above.

In a further preferred embodiment, the reaction mixture is also substantially free of carbon dioxide, urea and dialkyl-carbonates.

In a further preferred embodiment, the reaction mixture subjected to thermal treatment is composed of one or more diols having general formula (II) and is preferably composed of only one diol having general formula (II).

If the reaction mixture comprises only one diol having general formula (II), a compound having formula (I) is obtained as product, wherein Y is equal to Y'.

If the reaction mixture comprises two or more diols having general formula (II), the subsequent thermal treatment leads to the formation of four or more compounds having formula (I) mixed with each other.

In particular, if the reaction mixture comprises two diols having general formula (II), therefore having different substituents Z, indicated hereunder with Z' and Z", the subsequent thermal treatment leads to the formation of four products having formula (I):

a product wherein Y and Y' are equal to Z'
a product wherein Y and Y' are equal to Z"
a product wherein Y is equal to Z' and Y' is equal to Z"
a product wherein Y is equal to Z" and Y' is equal to Z'.

By treating, according to the present invention, a reaction mixture containing 3-methoxy-1,2-propanediol and 3-propoxy-1,2-propanediol, for example, a reaction mixture containing the following four products having formula (I) is obtained, wherein:

i) Y and Y' are a methoxy group,
ii) Y and Y' are a propoxy group,
iii) Y is a methoxy group and Y' is a propoxy group,
iv) Y is a propoxy group and Y' is a methoxy group.

The above mixture of products can be used as such as fuel component. Alternatively, the above compounds having formula (I) can be separated with techniques known to skilled persons in the field (e.g. distillation) and be used individually as fuel components.

The thermal treatment is carried out at a temperature within the range of 100° C.-300° C., preferably 150° C.-200° C.

The process allows conversions higher than 90% to be reached, even more preferably ranging from 95 to 100%. The completion of the reaction is determined by means of gaschromatographic analysis.

In formula (I), when Y is OR, R is, preferably, a linear or branched alkyl containing from 1 to 4 carbon atoms. R is preferably, ethyl, n-butyl, i-butyl, 3-methyl-1-butyl, 2-methyl-1-butyl. R is more preferably selected from ethyl and n-butyl.

The vicinal diol having formula (II) is preferably obtained starting from glycerine. Said glycerine is even more preferably obtained as by-product of a trans-esterification reaction of triglycerides, for example the reaction used in production processes of biodiesel or FAMEs.

The acid catalyst of the reaction can be selected from catalysts commonly used for esterification, etherification, alkylation or condensation reactions.

The catalyst is preferably selected from ion-exchange acid resins, zeolites in acid form, silica-aluminas and mixtures thereof.

The ion-exchange acid resins can be used directly in the form of microspheres, as normally available on the market. The acid zeolites and silica-aluminas are preferably extruded together with a binder.

Acid resins that can be used are those containing sulfonic or carboxylic acid groups.

Commercial resins such as, for example, Amberlyst 36, Amberlyst 70, Amberlite IR-120, Amberlite IRC-86, Amberlite IRC-50, can be used.

Zeolites that can be used are preferably medium- or large-pore zeolites, even more preferably zeolite Y, zeolite Beta or zeolite ZSM-5.

The zeolites are used in acid form, i.e. in the form in which the cationic sites present in their structure are occupied for at least 50% by hydrogen ions, and it is particularly preferable for at least 90% of the cationic sites to be occupied by hydrogen ions.

Silico-aluminas that can be used are those, for example, having a silica/alumina molar ratio ranging from 1/1 to 1,000/1, and even more preferably ranging from 20/1 to 200/1. Silico-aluminas that can be used are described, for example, in "Amorphous mesoporous silica-alumina with controlled pore size as acid catalysts", G. Bellussi, C. Perego, A. Carati, S. Peratello, E. Previde Massara, Studies in Surface Science and Catalysis, 84, 1994, 85-92.

Commercial silico-aluminas such as, for example, Siral 1, Siral 5, Siral 20, Siral 30, Siral 40, can also be used.

In a first preferred embodiment of the present invention, the starting vicinal diol is 1,2-propanediol, $HOCH_2-CHOH-CH_3$.

The compound 1,2-propanediol is preferably obtained by means of a catalytic hydrogenation process of glycerine with hydrogen, according to conventional methods known to skilled persons in the field.

Examples of catalysts that can be used in the hydrogenation reaction are: copper chromite, mixed oxides of chromium-zinc-copper, noble metals supported on carbon, noble metals supported on iron oxide, more preferably palladium on carbon, platinum on carbon, palladium on iron oxide and mixtures thereof.

The reduction reaction can be carried out at a temperature ranging from 100° C. to 250° C., under a hydrogen pressure ranging from 1 to 100 atm. As the starting glycerine is liquid, it is not necessary to use additional solvents in the reaction mixture. If desired, however, linear aliphatic alcohols can be used as solvents, or the same 1,2-propanediol that is to be obtained as product.

The hydrogenation reaction is preferably carried out in a fixed-bed catalytic reactor, feeding the reagents in a co-current or countercurrent mode. It is possible, however, to also use other reaction systems, such as, for example, an ebullated-bed reactor.

Mixtures of 1,2-propanediol and 1,3-propanediol are typically obtained from the above hydrogenation reaction, in which 1,2-propanediol is predominant with respect to 1,3-propanediol. Further by-products of this reaction can be ethylene glycol and methanol. The yield of the catalytic hydrogenation reaction is generally higher than 95%.

The mixture of 1,2-propanediol/1,3-propanediol is preferably subjected to separation, for example by distillation, to isolate the 1,2-propanediol in purified form.

Greater details relating to reduction processes that can be used for obtaining propanediol from glycerine are described, for example, in the article "*Selective hydrogenolysis of glycerol promoted by palladium*", Green Chemistry, 2009, 111, 1511-13, When the compound 1,2-propanediol is subjected to thermal treatment according to step (ii) of the present invention, in the presence of an acid catalyst, the compound 2-ethyl-4-methyl-1,3-dioxolane is obtained. This compound can be advantageously used as a fuel component, in particular for automotive vehicles, as it has an adequate hydrophobicity and compatibility with the hydrocarbon phase typical of fuels. When this compound is added to fuels, moreover, it reduces the emission of particulate deriving from their combustion.

In a second preferred embodiment of the present invention, the vicinal diol is a compound having formula (II) wherein Z is an OR' group, R' being a linear or branched alkyl containing from 1 to 8 carbon atoms.

Preferably, said compound, i.e. 3-alkoxy-1,2-propanediol, is obtained by means of an etherification process of glycerine with at least one alcohol, according to conventional methods. The etherification, for example, can be effected by reacting the glycerine with at least one alcohol in the presence of at least one acid catalyst.

Examples of acid catalysts that can be used for the etherification are: acid exchange resins, zeolites in acid form, silico-aluminas, supported phosphoric acid and mixtures thereof.

The acid exchange resins can be used directly in the form of microspheres, as normally available on the market. The acid zeolites and silica-alumina are preferably extruded together with a binder.

Solvents can also be used for the etherification reaction. In this case, the same alcohols used as reagents in the etherification reaction are preferably used as solvent.

The etherification reaction is preferably carried out at a temperature ranging from 50° C. to 200° C., and at a pressure ranging from 1 to 20 atm.

The space velocity of the reaction mixture on the catalyst preferably ranges from 0.1 to 20 $h^{-1}$.

The alcohol/glycerine molar ratio preferably ranges from 1 to 10.

The etherification reaction can be carried out, for example, in a fixed-bed catalytic reactor. In this case, the etherification in position 1 is favoured by the use of low contact times between the reaction mixture and catalyst.

The feeding of the reagents to the fixed-bed reactor can be effected in countercurrent or in co-current mode.

Alcohols having formula ROH are preferably used in the etherification reaction, wherein R is a linear or branched alkyl containing from 1 to 8 carbon atoms, preferably from 2 to 4 carbon atoms.

The alcohol is preferably selected from: ethanol, n-butanol, i-butanol, 3-methyl-1-butanol, 2-methyl-1-butanol or mixtures thereof. The alcohol is more preferably selected from: ethanol, n-butanol and mixtures thereof.

In particular, if the etherification reaction is carried out with a mixture of alcohols, it can lead to the formation of a mixture of diols, which can be used as such for the subsequent step or, more preferably, subjected to separation, for example by distillation, to isolate the vicinal diols having formula (II).

The alcohols used for the etherification are preferably obtained biologically, such as, for example, the alcohols obtained from the fermentation of biomasses or derivatives of biomasses, in particular biomasses deriving from agricultural crops rich in carbohydrates and sugars or from the fermentation of lignocellulosic or algal biomasses.

The lignocellulosic biomass can be obtained, for example, from agricultural crops rich in carbohydrates and sugars such as, for example, corn, sorghum, barley, beet, sugar cane, or mixtures thereof.

When the 3-alkoxy-1,2-propanediol is subjected to thermal treatment according to step (ii) of the present invention, in the presence of an acid catalyst, the compound 2-alkoxyethyl-4-alkoxymethyl-1,3-dioxolane is obtained, wherein the —OR alkoxy group has the meaning previously indicated for the compounds having formula (I).

When the compounds having formula (II) are subjected to thermal treatment according to the present invention, in the presence of an acid catalyst, compounds having formula (I) are obtained, wherein Y and Y', equal to or different from each other, are H or a OR group, R being a linear or branched alkyl containing from 1 to 8 carbon atoms.

The thermal treatment of thevicinal diol according to step (ii) of the present invention, can be effected using conventional equipment, known to the skilled persons in the field.

The thermal treatment, for example, can be effected in a fixed-bed reactor filled with catalyst (for example a fixed bed of an acid resin). The reaction can be also effected with other reaction systems, such as, for example, a Continuous Stirred-Tank Reactor (CSTR) or an ebullated-bed reactor.

The feeding of the reaction mixture comprising the vicinal diol on the catalyst, is preferably effected with a space velocity within the range of 0.1 to 12 $h^{-1}$.

The thermal treatment according to the invention is preferably carried out maintaining the reaction mixture in liquid phase. For this purpose, the reaction can be conducted keeping the reaction mixture containing the vicinal diol under pressure, in the reactor, for example at a pressure within the range of 1 to 50 atmospheres, even more preferably, from 1 to 20 atmospheres.

When the process according to the present invention is carried out under the above mentioned conditions, it is characterized by a substantially complete conversion of the starting vicinal diol and a selectivity towards the desired acetal up to 96%, the complement to 100% generally comprising the corresponding aldehyde, which can in any case be separated at the end of the reaction by means of distillation.

The process according to the present invention allows to overcome the drawbacks indicated by the state of the art. In particular, the process according to the present invention allows the acetals having formula (I) to be synthesized starting from a vicinal diol having formula (II) without using further chemical reagents, in particular without using aldehydes as additional reagent, according to what is described in WO2013/150457.

The present invention also allows the glycerine obtained as by-product of the trans-esterification reactions of triglycerides used in production processes of biofuels, to be exploited in a simple and economically convenient manner.

When the vicinal diols on which the process, object of the present invention, is applied, are obtained starting from glycerine obtained from renewable sources (e.g. trans-esterification of triglycerides contained in natural oils), compounds intrinsically of a vegetable origin are obtained, and they can therefore be used as components of a biological origin in biofuels in accordance with the international regulations in force.

The following embodiment example is provided for purely illustrative purposes of the present invention and should not be considered as limiting the protection scope defined in the enclosed claims.

EXAMPLE 1

(A) Synthesis of 1,2-propanediol 20 cc of cupric chromite (Sigma-Aldrich) are charged into a fixed-bed reactor and the reactor is heated to 250° C. in hydrogen. An equimolar mixture of glycerine and hydrogen is then fed at a space velocity of 1 $h^{-1}$ and samples of the mixture are collected, which are analyzed by means of gaschromatography.

The gaschromatographic analysis confirmed a substantially complete conversion of the glycerine, with a selectivity of about 97% to 1,2-propanediol, the complement to 100% consisting of propanol, ethylene glycol and methanol.

The catalyst is stable under the reaction conditions for over 200 hours, as there is no variation in either the conversion or the selectivity towards the desired product during this period of time.

The 1,2-propanediol obtained is separated from the reaction mixture by means of distillation.

(B) Synthesis of 2-ethyl-4-methyl-1,3-dioxolane 20 cc of acid resin Amberlyst 70 are charged into a fixed-bed reactor. After heating the reactor up to 180° C., 1,2-propanediol obtained according to Example 1 (A), is fed.

The feeding is effected at a space velocity of 0.5 $h^{-1}$. The reaction mixture is kept in liquid phase, applying a counter-pressure of 7 bar to the reactor.

Samples of the reaction mixture are collected during the reaction, and they are analyzed by means of gaschromatography.

The conversion of 1,2-propanediol to 2-ethyl-4-methyl-1,3-dioxolane is substantially complete with a selectivity of about 96% to the desired product, the complement to 100% consisting of propionic aldehyde, from which the desired product is separated by distillation.

The catalyst proves to be stable under the reaction conditions for over 300 hours, as there is no variation in either the conversion or the selectivity towards the desired product during this period of time.

The invention claimed is:

1. A process for preparing at least one compound having general formula (I):

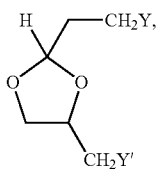

(I)

wherein Y and Y', the same or different, are selected from the group consisting of H and a group OR, R being a linear or branched alkyl containing from 1 to 8 carbon atoms,
  comprising at least the following phases:
  (i) providing a reaction mixture comprising at least a vicinal diol having formula (II)

$$Z-CH_2-CHOH-CH_2OH \qquad (II),$$

wherein Z is selected from the group consisting of H and a group OR', R' being a linear or branched alkyl containing from 1 to 8 carbon atoms, said mixture being substantially free of aldehydes having general formula $R^I-CHO$, wherein $R^I$ is a linear or branched alkyl containing from 1 to 6 carbon atoms, possibly substituted by an alkoxide group $OR^{III}$, wherein $R^{III}$ is an alkyl containing from 1 to 4 carbon atoms;
  (ii) thermally treating said reaction mixture at a temperature within the range of 100° C.-300° C. in the presence of at least one acid catalyst, obtaining said compound having formula (I), and
  wherein the thermally treating is carried out while maintaining said reaction mixture in liquid phase.

2. The process according to claim 1, wherein said temperature is within the range of 150° C.-200° C.

3. The process according to claim 1, wherein said R is a linear or branched alkyl containing from 1 to 4 carbon atoms.

4. The process according to claim 1, wherein R is selected from the group consisting of ethyl, n-butyl, i-butyl, 3-methyl-1-butyl, 2-methyl-1-butyl and mixtures thereof.

5. The process according to claim 1, wherein said acid catalyst is selected from the group consisting of: ion-exchange acid resin, acid zeolite, silica-alumina and mixtures thereof.

6. The process according to claim 1, wherein said vicinal diol is obtained starting from glycerine.

7. The process according to claim 6, wherein said vicinal diol is 1,2-propanediol.

8. The process according to claim 7, further comprising obtaining said 1,2-propanediol by a catalytic hydrogenation process of glycerine with hydrogen.

9. The process according to claim 8, further comprising purifying by distillation said 1,2-propanediol obtained by means of said hydrogenation reaction before said thermal treatment.

10. The process according to claim 1, wherein said vicinal diol is obtained by means of an etherification process of glycerine with at least one alcohol.

11. The process according to claim 10, wherein said at least one alcohol is selected from the group consisting of: ethanol, n-butanol, i-butanol, 3-methyl-1-butanol, 2-methyl-1-butanol and mixtures thereof.

12. The process according to claim 6, wherein said glycerine is obtained from a trans-esterification reaction of triglycerides.

13. The process according to claim 1, wherein $R^I$ is a linear or branched alkyl containing from 1 to 6 carbon atoms that is substituted by an alkoxide group $OR^{III}$, wherein $R^{III}$ is an alkyl containing from 1 to 4 carbon atoms.

14. The process according to claim 1, wherein R is ethyl or n-butyl or mixtures thereof.

15. The process according to claim 10, said at least one alcohol is ethanol, n-butanol or mixtures thereof.

\* \* \* \* \*